Feb. 22, 1955 R. O. RUBEL, JR Plant Pat. 1,350
CAMELLIA PLANT
Filed Sept. 16, 1953
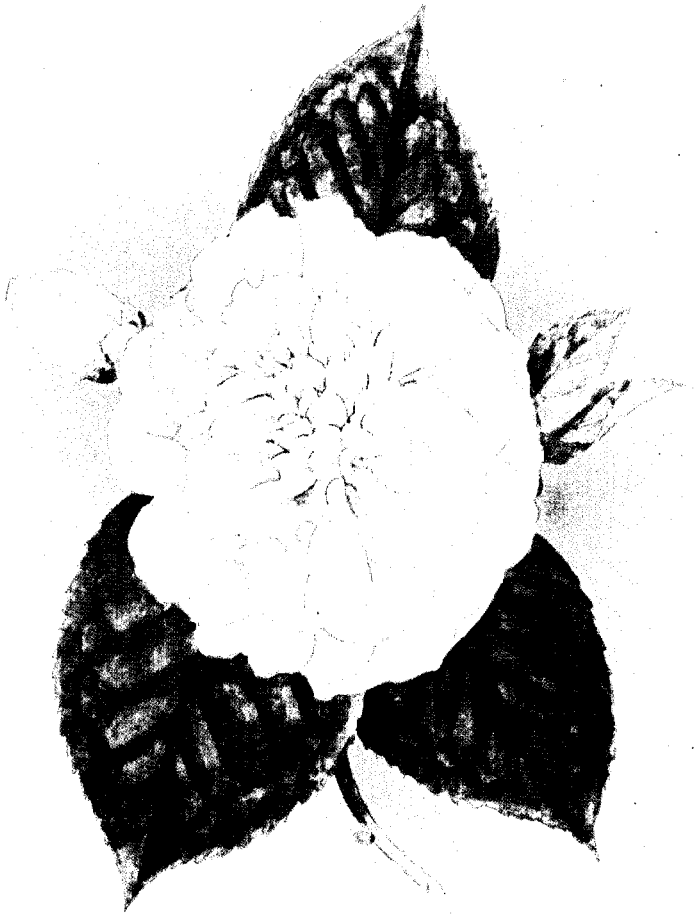
WITNESS
Addison E. Avery
INVENTOR
ROBERT O. RUBEL, JR.
by Rummler, Rummler & Snow,
ATTYS.

United States Patent Office

Plant Pat. 1,350
Patented Feb. 22, 1955

1,350

CAMELLIA PLANT

Robert O. Rubel, Jr., Mobile, Ala., assignor to Cliff Harris, Mobile, Ala.

Application September 16, 1953, Serial No. 380,634

1 Claim. (Cl. 47—60)

This invention relates to a new and distinct variety of camellia plant. It was the result of selection procedure with seedlings obtained by harvesting, and growing seeds from selected parent plants. This variety originated from seed planted in 1932 in my garden at Mobile, Alabama.

Its immediate parentage is unknown. It compares slightly with the variety known as "Debutante" (unpatented). Its blooms are considerably larger and of greater depth and their color is slightly darker.

The plant has been asexually reproduced by cuttings and graftings at Mobile, Alabama, and its features remain true to form and color.

The blooms are unicolored, opening a light salmon pink and changing to a medium rose pink as the flower ages. Some sport plants have been produced with white variegations by grafting one scion of this variety and one scion of a pure white variety on the same understock. A sport bloom with white variegations has appeared on the grafted scion of the parent plant. No other sport has occurred on the parent plant.

The accompanying painting shows the bloom and foliage of this new camellia in its natural colors.

A detailed description follows:

Parentage: Seedling. Seed parent unknown.
Classification: *Camellia japonica.*
Propagation: Reproduced asexually from cuttings and grafting.
Plant: Form—round bush. Height depends on age, compact and vigorous growth, and branching.
Flower:
*Recurrent.*—Yes.
*Blooms.*—Early to late. Produces sports variegated with white.
*Size.*—Maximum size 5 in. (12.7 cm.) in diameter.
*Borne.*—Both singly and double.
*Shape.*—Incomplete double with high center.
*Petalage.*—152 petals and petaloids of which 22 are large guard petals. The remainder are smaller petals and petaloids, the latter being in clustered formation in center and some slightly variegated with white.
Outer petals in 3 rows, large, approximately 2 in. (5 cm.) long x 1 14/16 in. (4.8 cm.) wide, self colored.
Orbicular in shape, lobed at apex, attenuate at base; lower portions crimped; haft short and narrow.

Texture—leathery; appearance, satiny.
Affected by hot weather 60° or above.
Lasting quality on plant and as a cut flower excellent.
Bud:
*Size.*—Large, 1 3/16 in. (3 cm.) long and 13/16 in. (2 cm.) in diameter just before opening.
*Form.*—Elliptic ovoid. Cup-shaped.
*Sepals.*—Hooded approximately ⅔ over bud.
Color—outer sepals light green with narrow tan margins; inner ones, thin, dark green.
Number of sepals, 9.
Calyx: Form—flat, 1 13/16 in. (4.5 cm.) across. Doesn't split. Aspect—smooth.
Genital organs:
*Stamens.*—18–30 in center with very short filaments.
Color—very light rose tint.
Arrangement—clustered in fascicles.
*Pistil.*—Malformed.
*Styles.*—4–5 in number. 13/16 in. (2 cm.) in length.
*Ovary.*—Glabrous.
Foliage: Abundant in quantity. Leaves coriaceous, ovate in shape, blades approximately 2 15/16 in.–4⅛ in. (7.5–10.5 cm.) x 1 9/16–2 3/16 in. (4–5.5 cm.) wide. Bases, cuneate, apexes acute, sometimes acuminate.
*Color.*—Upper side, blue-green. Under side, yellow-green.
*Petioles.*—Approximately 13/16 in. (2 cm.)
Fruit: Fertile. Form—usually ovoid and green in color.

The color designations according to Maerz and Paul's Dictionary of Color are as follows:

| | Plate | Lts. | No. |
|---|---|---|---|
| Flower: | | | |
| Lightest shade | 1 | E | 4. |
| shading into | 1 | I | 4. |
| shading into (darkest tone) | 1 | J | 4. |
| Pistils or stamens: (yellow) | 9 | L | 7. |
| Leaves: | | | |
| Top side of leaf | 21 | L | 7 plus yellow. |
| Under side of leaf (not shown in drawing). | 20 | L | 6 plus yellow. |
| A flat leaf, pronounced serrated edge with light colored center and side rib and veins, no high lights, because of flatness and lack of gloss on leaf. | | | |
| Stem | 7 | C | 12. |

At my nursery in Mobile, Alabama, these plants produce flowers in November and continue blooming through February. The blooms are especially suitable for corsages and florists' cut flowers. The plant is hardy and has continued to bloom with good flowers after enduring freezing weather while growing outside unprotected.

I claim:

The new and distinct variety of camellia plant, substantially as herein shown and described, characterized as to novelty by its large deep blooms of distinctive shape and color, and its early to late blooming period and its ability to withstand freezing weather.

No references cited.